United States Patent [19]

Baus et al.

[11] Patent Number: 5,047,551
[45] Date of Patent: Sep. 10, 1991

[54] PREPARATION OF 4-CHLOROPYRAZOLES

[75] Inventors: Ulf Baus, Dossenheim; Wolfgang Reuther, Heidelberg, both of Fed. Rep. of Germany

[73] Assignee: BASF Aktiengesellschaft, Ludwigshafen, Fed. Rep. of Germany

[21] Appl. No.: 429,783

[22] Filed: Oct. 30, 1989

[30] Foreign Application Priority Data

Nov. 30, 1988 [DE] Fed. Rep. of Germany ....... 3840342

[51] Int. Cl.$^5$ ........................................... C07D 231/14
[52] U.S. Cl. .................... 548/375; 548/376
[58] Field of Search ............................... 548/375, 376

[56] References Cited

FOREIGN PATENT DOCUMENTS 1670060 3/1966 Fed. Rep. of Germany ...... 548/375

OTHER PUBLICATIONS

Liebigs Annalen der Chemie, 598 (1956), pp. 186–197.

Primary Examiner—Mary C. Lee
Assistant Examiner—Robert C. Whittenbaugh
Attorney, Agent, or Firm—John H. Shurtleff

[57] ABSTRACT

4-Chloropyrazoles of the general formula I

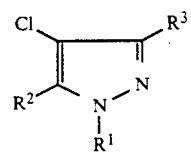

where $R^1$, $R^2$ and $R^3$ are each independently of the others hydrogen or a radical which is inert under the reaction conditions, are prepared by reacting pyrazoles of the general formula II

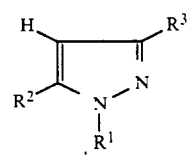

wherein $R^1$, $R^2$ and $R^3$ are each as defined above, with 0.95–10 equivalents of hypochloric acid, or salts thereof, in the substantial absence of any carboxylic acid.

12 Claims, No Drawings

PREPARATION OF 4-CHLOROPYRAZOLES

The present invention relates to an improved process for preparing 4-chloropyrazoles from pyrazoles.

Liebigs Ann. Chem. 598 (1956), 186-197, discloses the reaction of pyrazole with a 9% strength solution of NaOCl in the presence of acetic acid to give 4-chloropyrazole in a 70% yield. The disadvantage of this method is the use of acetic acid and the unsatisfactory yield.

It is an object of the present invention to provide an improved process for preparing 4-chloropyrazoles and to eliminate the disadvantages.

We have found that this object is achieved by an improved process for preparing a 4-chloropyrazole of the general formula I

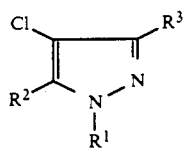

where $R^1$, $R^2$ and $R^3$ are each independently of the others hydrogen or a radical which is inert under the reaction conditions, which comprises reacting a pyrazole of the general formula II

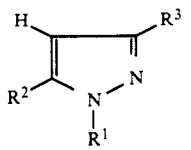

wherein $R^1$, $R^2$ and $R^3$ are each as defined above, with 0.95-10 equivalents of hypochloric acid, or a salt thereof, in the substantial absence of any carboxylic acid.

A 4-chloropyrazole I is obtainable by the following method:

The reaction takes place between a pyrazole II, which has hydrogen in the 4-position, and hypochloric acid, or a salt thereof, at from $-20°$ to $+70°$ C. in the substantial absence of any carboxylic acid in a suitable solvent in accordance with the following equation:

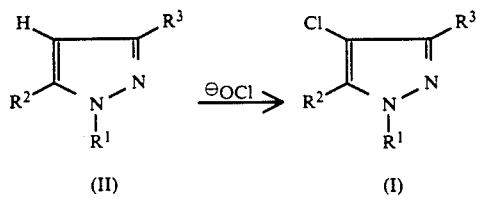

The reaction is preferably carried out at $0°-40°$ C., particularly preferably at $5°-30°$ C.

Compounds of the formula II are partly known from Liebigs Ann. Chem., loc. cit., or they can be prepared as described therein or in DE-A-1,670,060.

The hypochloric acid, or a salt thereof, is used in 0.95-10 equivalents based on compound II, preferably 0.99-2, particularly preferably 1-1.5; that is, the molar ratio between hypochloric acid or a salt thereof, and compound II is from 0.95:1 to 10:1, preferably from 0.99:1 to 2:1, particularly preferably from 1:1 to 1.5:1.

By "in the substantial absence of any carboxylic acid" is meant that the reaction mixture may contain from 0 to 0.5% by weight, preferably from 0 to 0.2% by weight, of a carboxylic acid, but is particularly preferably carried out in the absence of any carboxylic acid.

Suitable solvents for the reaction are ketones such as acetones, acyclic and cyclic ethers such as tetrahydrofuran, glycols such as ethylene glycol and propylene glycol, and glycol ethers such as diglyme, or mixtures thereof with water, but preference is given to water.

In the course of the workup, the reaction mixture is adjusted to pH 7-14, preferably pH 8-12, particularly preferably pH 9-11.

Suitable extractants are ethers such as diethyl ether and methyl tert-butyl ether, esters such as methyl acetate and ethyl acetate, aromatic hydrocarbons such as benzene, toluene and the xylenes, chlorohydrocarbons such as methylene chloride and chloroform, and mixtures thereof, but preference is given to the abovementioned esters and ethers.

The substituents $R^1$, $R^2$ and $R^3$ in the formulae I and II are each independently of the others hydrogen or a radical which is inert under the reaction conditions. Such radicals are $C_1-C_8$-alkyl such as methyl, ethyl, n-propyl, isopropyl, n-butyl, isobutyl, sec-butyl, tert-butyl, pentyl, hexyl, heptyl or octyl, and $C_1-C_4$-haloalkyl such as $C_1-C_4$-chloroalkyl or -fluoroalkyl, e.g. fluoromethyl, difluoromethyl, trifluoromethyl, chloromethyl, dichloromethyl, trichloromethyl, chlorofluoromethyl, 2,2,2-trifluoroethyl or 2,2,2-trichloroethyl, preference being given to methyl and ethyl.

Of the compounds I and II, the following are preferred: 4-chloropyrazole, 4-chloro-N-methylpyrazole, 4-chloro-3,5-dimethylpyrazole, 4-chloro-3-methylpyrazole, 3-methylpyrazole, pyrazole, N-methylpyrazole and 3,5-dimethylpyrazole.

4-Chloropyrazoles are intermediates for preparing active substances, for example biocides (DE-A-3,412,080). 4-Chloropyrazole itself can be used for example as a pharmaceutically active substance in the control of epileptic conditions.

EXAMPLE 34 g (0.5 mol) of pyrazole were suspended in 100 ml of water. 425 g (0.5 mol) of an aqueous 8.7% strength by weight NaOCl solution were added dropwise with continuous stirring in such a way that the temperature of the reaction mixture did not exceed 30° C. The reaction was monitored by HPLC analysis. After the reaction had ended, 35% strength sulfuric acid was added, and the mixture was extracted at pH 11 with 300 ml of ethyl acetate. The combined organic phases were dried and the solvent was removed under reduced pressure, leaving the 4-chloropyrazole as slightly yellow crystals.

Yield: 51 g (0.5 mol, 99%).

Elemental analysis of crude product: calculated: C 35.1, H 2.9, N 27.3, Cl 34.5. found: C 35.2, H 3.4, N 26.9, Cl 33.6.

We claim:

1. A process for preparing a 4-chloropyrazole of the formula

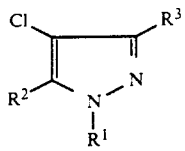

where $R^1$, $R^2$ and $R^3$ are each independently of the others hydrogen or a substituent which is inert under the reaction conditions and selected from the group consisting of $C_1$-$C_8$-alkyl and halosubstituted $C_1$-$C_4$-alkyl, which process comprises:

reacting a pyrazole of the formula

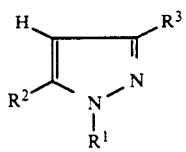

where $R^1$, $R^2$ and $R^3$ are each as defined above, in a solvent medium with 0.95-10 equivalents of hypochloric acid, or a salt thereof, while excluding any carboxylic acid in an amount more than about 0.5% by weight, calculated as acetic acid and based on the weight of the reaction mixture; and isolating the product I.

2. A process as claimed in claim 1, wherein a carboxylic acid is excluded in amounts of more than about 0.2%, calculated as acetic acid and based on the weight of the reaction mixture.

3. A process as claimed in claim 1, wherein the reaction mixture is essentially free of any carboxylic acid.

4. A process as claimed in claim 1, wherein the reaction is carried out in an aqueous medium and the product is isolated at a pH of 7-14.

5. A process as claimed in claim 4, wherein the product is isolated at a pH of 8-12.

6. A process as claimed in claim 4, wherein the product is isolated at a pH of 9-11.

7. A process as claimed in claim 1, wherein the reaction is carried out in a solvent medium consisting essentially of water.

8. A process as claimed in claim 1, wherein the reaction is carried out at a temperature of from −20° to 70° C.

9. A process as claimed in claim 8, wherein the reaction is carried out at 0°-40° C.

10. A process as claimed in claim 8, wherein the reaction is carried out at 5°-30° C.

11. A process as claimed in claim 1, wherein the product I is isolated by extraction from the reaction mixture with an extractant selected from the group consisting of ethers, esters, aromatic hydrocarbons, chlorohydrocarbons and mixtures thereof.

12. A process as claimed in claim 1, wherein the extractant is selected from the group consisting of diethyl ether, methyl tert.-butyl ether, methyl acetate, ethyl acetate and mixtures thereof.

* * * * *